United States Patent
Seddon et al.

(10) Patent No.: US 10,864,069 B2
(45) Date of Patent: *Dec. 15, 2020

(54) STENT WITH DEFLECTING CONNECTOR

(71) Applicant: BOSTON SCIENTIFIC SCIMED, INC., Maple Grove, MN (US)

(72) Inventors: Dane T. Seddon, Boston, MA (US); Daniel Ross, Watertown, MN (US); Burns P. Doran, Monticello, MN (US); Sean P. Fleury, Minneapolis, MN (US); Mark D. Wood, Sterling, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 275 days.

This patent is subject to a terminal disclaimer.

(21) Appl. No.: 15/884,790

(22) Filed: Jan. 31, 2018

(65) Prior Publication Data

US 2018/0147043 A1 May 31, 2018

Related U.S. Application Data

(63) Continuation of application No. 14/310,481, filed on Jun. 20, 2014, now Pat. No. 9,907,640.

(60) Provisional application No. 61/837,770, filed on Jun. 21, 2013.

(51) Int. Cl.
*A61F 2/04* (2013.01)
*A61F 2/915* (2013.01)
*A61F 2/91* (2013.01)

(52) U.S. Cl.
CPC ................. *A61F 2/04* (2013.01); *A61F 2/91* (2013.01); *A61F 2/915* (2013.01); *A61F 2002/046* (2013.01); *A61F 2002/91575* (2013.01)

(58) Field of Classification Search
CPC ........ A61F 2002/046; A61F 2/04; A61F 2/91; A61F 2/915
See application file for complete search history.

(56) References Cited

U.S. PATENT DOCUMENTS

| | | | |
|---|---|---|---|
| 5,513,240 | A | 4/1996 | Hausmann et al. |
| 5,629,972 | A | 5/1997 | Hausmann et al. |
| 5,759,192 | A | 6/1998 | Saunders |
| 5,776,161 | A | 7/1998 | Globerman |
| 5,780,807 | A | 7/1998 | Saunders |
| 5,843,117 | A | 12/1998 | Alt et al. |

(Continued)

FOREIGN PATENT DOCUMENTS

| | | |
|---|---|---|
| DE | 10150547 A1 | 4/2003 |
| JP | 2005524488 A | 8/2005 |

(Continued)

OTHER PUBLICATIONS

Boston Scientific Launches 2.25 mm Promus Coronary Stent, Diagnostic and Interventional Cardioloogy, www.bostonscientific.com, May 25, 2011.
Colombo et al., Selection of Coronary Stents, JACC, Sep. 18, 2002, vol. 40, No. 6, Elzevier Science Inc.
Ielasi et al., Current and Future Drug-eluting Coronary Stent Technology, Expert Reviews Cardiovascular Therapy, 2011, 9(4): 485-503, http://www.medscape.com/viewarticle/742008—print.

(Continued)

*Primary Examiner* — Gregory A Anderson
(74) *Attorney, Agent, or Firm* — Seager, Tufte & Wickhem, LLP

(57) ABSTRACT

This disclosure is directed primarily to a stent for use in the trachea. The stent has a nominally deployed state, an axially extended state and an axially compressed state. The stent has a length. In the axially extended state, the length is at least 20% greater than in the nominally deployed state.

20 Claims, 5 Drawing Sheets

(56) References Cited

U.S. PATENT DOCUMENTS

| | | |
|---|---|---|
| 5,855,600 A | 1/1999 | Alt |
| 6,042,597 A | 3/2000 | Kveen et al. |
| 6,066,169 A | 5/2000 | McGuinness |
| 6,159,237 A | 12/2000 | Alt et al. |
| 6,183,506 B1 | 2/2001 | Penn et al. |
| 6,217,608 B1 | 4/2001 | Penn et al. |
| 6,231,598 B1 | 5/2001 | Berry et al. |
| 6,245,101 B1 | 6/2001 | Drasler et al. |
| 6,290,720 B1 | 9/2001 | Khosravi et al. |
| 6,312,460 B2 | 11/2001 | Drasler et al. |
| 6,375,677 B1 | 4/2002 | Penn et al. |
| 6,464,720 B2 | 10/2002 | Boatman et al. |
| 6,464,723 B1 | 10/2002 | Callol |
| 6,475,237 B2 | 11/2002 | Drasler et al. |
| 6,506,211 B1 | 1/2003 | Skubitz et al. |
| 6,585,755 B2 | 7/2003 | Jackson et al. |
| 6,616,689 B1 | 9/2003 | Ainsworth et al. |
| 6,629,994 B2 | 10/2003 | Gomez et al. |
| 6,635,083 B1 | 10/2003 | Cheng et al. |
| 6,641,609 B2 | 11/2003 | Globerman |
| 6,656,220 B1 | 12/2003 | Gomez et al. |
| 6,712,843 B2 | 3/2004 | Elliott |
| 6,723,118 B1 | 4/2004 | Ballou et al. |
| 6,758,860 B1 | 7/2004 | Penn et al. |
| 6,767,360 B1 | 7/2004 | Alt et al. |
| 6,776,794 B1 | 8/2004 | Hong et al. |
| 6,790,227 B2 | 9/2004 | Burgermeister |
| 6,796,997 B1 | 9/2004 | Penn et al. |
| 6,858,037 B2 | 2/2005 | Penn et al. |
| 6,881,223 B2 | 4/2005 | Penn et al. |
| 6,887,264 B2 | 5/2005 | Penn et al. |
| 6,896,696 B2 | 5/2005 | Doran et al. |
| 6,929,660 B1 | 8/2005 | Ainsworth et al. |
| 6,939,373 B2 | 9/2005 | Gomez et al. |
| 6,942,689 B2 | 9/2005 | Majercak |
| 6,942,690 B1 | 9/2005 | Pollock et al. |
| 6,955,686 B2 | 10/2005 | Majercak et al. |
| 7,004,968 B2 | 2/2006 | Lootz et al. |
| 7,025,777 B2 | 4/2006 | Moore |
| 7,094,255 B2 | 8/2006 | Penn et al. |
| 7,112,216 B2 | 9/2006 | Gregorich |
| 7,122,049 B2 | 10/2006 | Banas et al. |
| 7,128,756 B2 | 10/2006 | Lowe et al. |
| 7,141,062 B1 | 11/2006 | Pinchasik et al. |
| 7,153,322 B2 | 12/2006 | Alt |
| 7,179,286 B2 | 2/2007 | Lenz |
| 7,179,289 B2 | 2/2007 | Shanley |
| 7,247,166 B2 | 7/2007 | Pienknagura |
| 7,397,935 B2 | 7/2008 | Kimmel et al. |
| 7,455,753 B2 | 11/2008 | Roth |
| 7,599,727 B2 | 10/2009 | Teichman et al. |
| 7,632,301 B2 | 12/2009 | Alt |
| 7,645,297 B2 | 1/2010 | Nissl |
| 7,674,416 B2 | 3/2010 | Hong et al. |
| 7,686,843 B2 | 3/2010 | Moore |
| 7,691,461 B1 | 4/2010 | Prabhu |
| 7,740,653 B1 | 6/2010 | Pollock et al. |
| 7,763,067 B2 | 7/2010 | Bales et al. |
| 7,766,958 B2 | 8/2010 | Alt et al. |
| 7,780,721 B2 | 8/2010 | Bales et al. |
| 7,846,179 B2 | 12/2010 | Belef et al. |
| 7,896,912 B2 | 3/2011 | Shanley |
| 7,938,854 B2 | 5/2011 | Stinson et al. |
| 7,951,188 B2 | 5/2011 | Ainsworth et al. |
| 7,959,999 B2 | 6/2011 | Prabhu |
| 7,980,289 B2 | 7/2011 | Banas et al. |
| 7,988,719 B2 | 8/2011 | Alt et al. |
| 7,988,720 B2 | 8/2011 | Brown et al. |
| 8,007,605 B2 | 8/2011 | Arbefeuille et al. |
| 8,012,195 B2 | 9/2011 | Jang |
| 8,016,873 B1 | 9/2011 | Drasler et al. |
| 8,048,142 B2 | 11/2011 | Venturelli |
| 8,070,794 B2 | 12/2011 | Issenmann |
| 8,075,609 B2 | 12/2011 | Penn et al. |
| 8,114,149 B2 | 2/2012 | Fischell et al. |
| 8,292,944 B2 | 10/2012 | Schmid et al. |
| 8,323,331 B2 | 12/2012 | Dreher |
| 2001/0007955 A1 | 7/2001 | Drasler et al. |
| 2001/0027339 A1 | 10/2001 | Boatman et al. |
| 2002/0002400 A1 | 1/2002 | Drasler et al. |
| 2002/0010504 A1 | 1/2002 | Alt |
| 2002/0042645 A1 | 4/2002 | Shannon |
| 2002/0123798 A1 | 9/2002 | Burgermeister |
| 2002/0165605 A1 | 11/2002 | Penn et al. |
| 2002/0169501 A1 | 11/2002 | Penn et al. |
| 2002/0177892 A1 | 11/2002 | Globerman |
| 2002/0183832 A1 | 12/2002 | Penn et al. |
| 2002/0198589 A1 | 12/2002 | Leong |
| 2002/0198593 A1 | 12/2002 | Gomez et al. |
| 2003/0004563 A1 | 1/2003 | Jackson et al. |
| 2003/0009214 A1 | 1/2003 | Shanley |
| 2003/0018380 A1 | 1/2003 | Craig et al. |
| 2003/0028239 A1 | 2/2003 | Dong |
| 2003/0159920 A1 | 8/2003 | Roth |
| 2003/0167085 A1 | 9/2003 | Shanley |
| 2003/0176914 A1 | 9/2003 | Rabkin et al. |
| 2003/0199968 A1 | 10/2003 | Ainsworth et al. |
| 2004/0024444 A1 | 2/2004 | Moore |
| 2004/0024445 A1 | 2/2004 | Dickson |
| 2004/0039439 A1 | 2/2004 | Gomez et al. |
| 2004/0122505 A1 | 6/2004 | Shanley |
| 2004/0153141 A1 | 8/2004 | Penn et al. |
| 2004/0186554 A1 | 9/2004 | Banas et al. |
| 2004/0215325 A1 | 10/2004 | Penn et al. |
| 2004/0225350 A1 | 11/2004 | Shanley |
| 2004/0236404 A1 | 11/2004 | Penn et al. |
| 2004/0254632 A1 | 12/2004 | Alt et al. |
| 2005/0043782 A1 | 2/2005 | Gomez et al. |
| 2005/0070991 A1 | 3/2005 | Pienknagura |
| 2005/0107864 A1 | 5/2005 | Hong et al. |
| 2005/0113909 A1 | 5/2005 | Shannon et al. |
| 2005/0222671 A1 | 10/2005 | Schaeffer et al. |
| 2005/0249391 A1 | 11/2005 | Kimmel et al. |
| 2006/0015138 A1 | 1/2006 | Gertner |
| 2006/0015173 A1 | 1/2006 | Clifford et al. |
| 2006/0036312 A1 | 2/2006 | Tomonto |
| 2006/0060266 A1 | 3/2006 | Bales et al. |
| 2006/0064154 A1 | 3/2006 | Bales et al. |
| 2006/0064155 A1 | 3/2006 | Bales et al. |
| 2006/0064158 A1 | 3/2006 | Bales et al. |
| 2006/0074480 A1 | 4/2006 | Bales et al. |
| 2006/0136041 A1 | 6/2006 | Schmid et al. |
| 2006/0184233 A1 | 8/2006 | Moore |
| 2006/0200228 A1 | 9/2006 | Penn et al. |
| 2006/0229711 A1 | 10/2006 | Yan et al. |
| 2006/0287706 A1 | 12/2006 | Olsen et al. |
| 2007/0010870 A1 | 1/2007 | Alt et al. |
| 2007/0031584 A1 | 2/2007 | Roth |
| 2007/0049970 A1 | 3/2007 | Belef et al. |
| 2007/0073134 A1 | 3/2007 | Teichman et al. |
| 2007/0077347 A1 | 4/2007 | Richter |
| 2007/0088430 A1 | 4/2007 | Banas et al. |
| 2007/0163668 A1 | 7/2007 | Arbefeuille et al. |
| 2007/0213810 A1 | 9/2007 | Newhauser et al. |
| 2008/0021536 A1 | 1/2008 | Penn et al. |
| 2008/0021542 A1 | 1/2008 | Penn et al. |
| 2008/0125854 A1 | 5/2008 | Alt et al. |
| 2008/0132997 A1 | 6/2008 | Venturelli |
| 2008/0154353 A1 | 6/2008 | Nissl |
| 2008/0188924 A1 | 8/2008 | Prabhu |
| 2008/0208319 A1 | 8/2008 | Rabkin et al. |
| 2008/0285720 A1 | 11/2008 | Bill et al. |
| 2009/0036974 A1 | 2/2009 | Penn et al. |
| 2009/0143853 A1 | 6/2009 | Morris et al. |
| 2009/0163980 A1 | 6/2009 | Stevenson |
| 2009/0192590 A1 | 7/2009 | Penn et al. |
| 2010/0057190 A1 | 3/2010 | Issenmann |
| 2010/0070021 A1 | 3/2010 | Wack et al. |
| 2010/0137973 A1 | 6/2010 | Sutermeister et al. |
| 2010/0174358 A1 | 7/2010 | Rabkin et al. |
| 2010/0193483 A1 | 8/2010 | Chen et al. |
| 2010/0249903 A1 | 9/2010 | Wack et al. |
| 2010/0256739 A1 | 10/2010 | Tippett et al. |
| 2010/0262226 A1 | 10/2010 | Dreher |

(56) References Cited

U.S. PATENT DOCUMENTS

| | | |
|---|---|---|
| 2010/0286464 A1 | 11/2010 | Chisick et al. |
| 2011/0066227 A1 | 3/2011 | Meyer et al. |
| 2011/0190871 A1 | 8/2011 | Trollsas et al. |
| 2011/0196475 A1 | 8/2011 | Kitaoka et al. |
| 2011/0208288 A1 | 8/2011 | Arbefeuille et al. |
| 2011/0213458 A1 | 9/2011 | Ainsworth et al. |
| 2011/0238152 A1 | 9/2011 | Richter |
| 2011/0245659 A1 | 10/2011 | Ma et al. |
| 2011/0257723 A1 | 10/2011 | McNamara |
| 2011/0276125 A1 | 11/2011 | Walker et al. |
| 2011/0319978 A1 | 12/2011 | Schaffer |
| 2012/0004718 A1 | 1/2012 | Craig et al. |
| 2012/0065723 A1 | 3/2012 | Drasler et al. |
| 2012/0078347 A1 | 3/2012 | Braido et al. |
| 2012/0179238 A1 | 7/2012 | Sarac et al. |
| 2012/0239142 A1 | 9/2012 | Liu et al. |
| 2013/0023981 A1 | 1/2013 | Dierking et al. |

FOREIGN PATENT DOCUMENTS

| | | |
|---|---|---|
| JP | 2008544765 A | 12/2008 |
| JP | 2009522022 A | 6/2009 |
| WO | 03094798 A1 | 11/2003 |
| WO | 2006108010 A2 | 10/2006 |
| WO | 2007079363 A2 | 7/2007 |
| WO | 2009103011 A1 | 8/2009 |
| WO | 2010088776 A1 | 8/2010 |

OTHER PUBLICATIONS

Notification of Transmittal of the International Search Report and the Written Opinion of the International Searching Authority, or the Declaration, for PCT Application No. PCT/US2014/43406, dated Oct. 1, 2014.

Ormiston, et al., Stent Longitudinal Integrity, Bench Insights Into a Clinical Problem, JACC: Cardiovascular Interventions, Nov. 7, 2011, vol. 4, No. 12, Elzevier Science Inc.

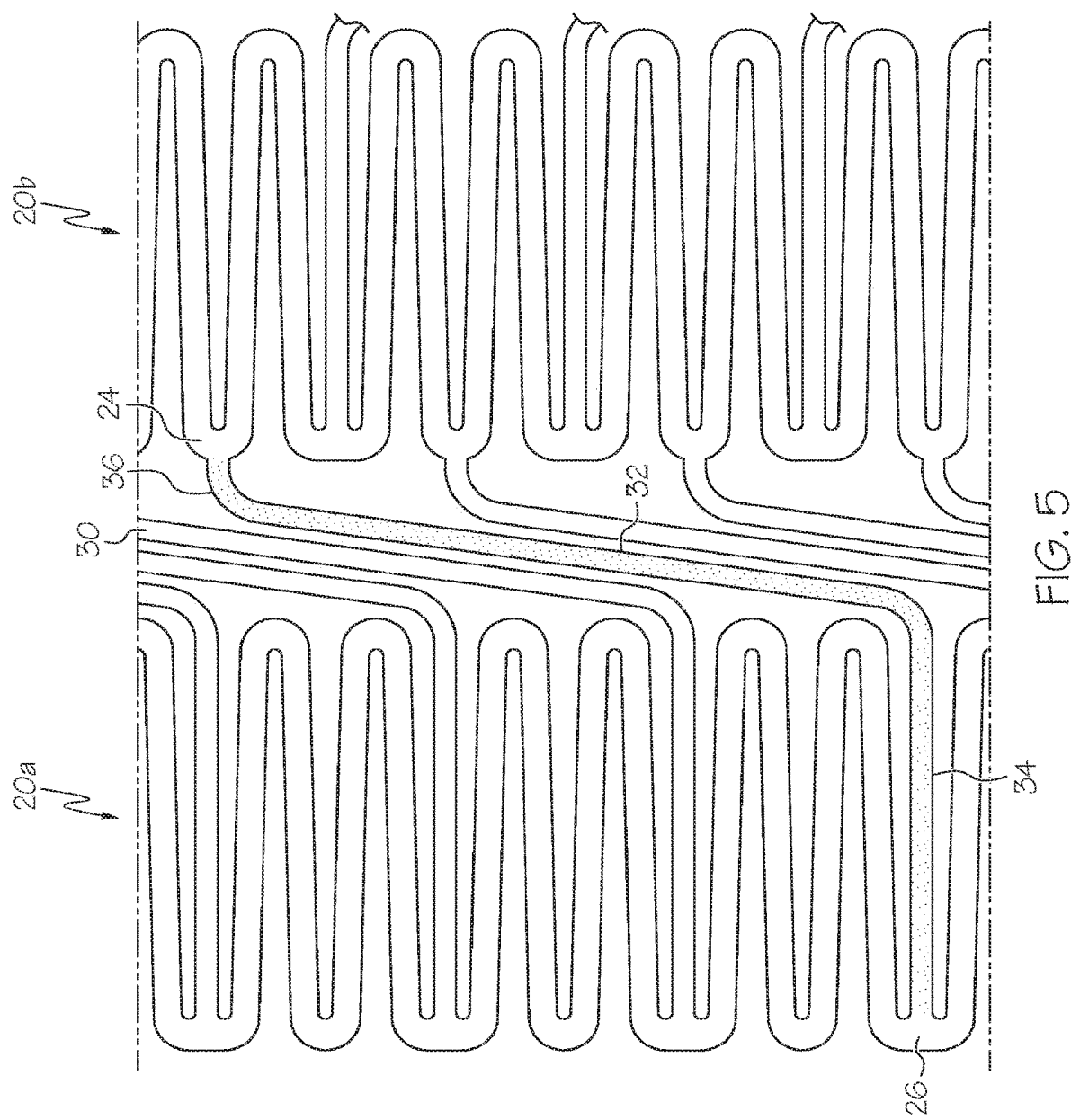

STENT WITH DEFLECTING CONNECTOR

CROSS-REFERENCE TO RELATED APPLICATIONS

This Application is a continuation of U.S. application Ser. No. 14/310,481, filed Jun. 20, 2014, which claims the benefit of and priority to U.S. Provisional Application No. 61/837,770, filed Jun. 21, 2013, which is herein incorporated by reference.

BACKGROUND

A stent is a medical device introduced into a body lumen. A stent is typically delivered in an unexpanded state to a desired location in a bodily lumen and then expanded by an internal radial force. Stents, grafts, stent-grafts, vena cava filters, expandable frameworks, and similar implantable medical devices, collectively referred to hereinafter as stents, are radially expandable endoprostheses, which are typically intravascular implants capable of being implanted transluminally.

Stents have previously been introduced into the trachea in order to address a variety of medical issues: to provide additional support to the trachea itself and/or the surrounding tissue following surgery, to prevent the airway from being constricted from tumor in growth, to alleviate stenosis, etc.

Tracheal stents face a unique environment of use, one in which the deployed stent must expand and contract during respiration and also be capable of providing support to the trachea.

When referring to tracheal stents, removability and flexibility are often the two things physicians speak about when referring to a great stent. Removability allows the physician the option to place a stent with confidence in treatable malignant conditions, as well as benign conditions, without the dangers of leaving an implant behind. Flexibility of a stent translates to comfort for a patient, e.g., a stent that does not force the lumen in to a straightened path offers reduced irritation. This disclosure will describe stents having geometries which exhibit both of these properties.

SUMMARY

As mentioned above, embodiments of the present disclosure are directed to stents and stent geometries which provide improved flexibility and removability characteristics. Some embodiments are directed to stents for use in a mammalian trachea.

As mentioned above, embodiments of the stent disclosed herein are provided with geometries that provide the stent with desired tracheal flexiblility as well as allow the stent to be readily removed from the trachea following either short-term or long term deployment.

Removability: The stent geometry is designed in such a way that it allows axial extension and compression to mimic the anatomical environment's extreme conditions. The connectors of the embodiments disclosed herein are configured to be in tension with one another and provide minimal diameter shift, direct pull force translation, and increased durability. These features are improvements over known stents in that prior stents are known to fracture and pull apart if there is significant tissue in-growth anchoring the stent to the anatomy; this is due to the stent cells distorting beyond the designed intent and inducing high stress regions. In the arrangements of the stent connectors shown and described herein, the stress concentration is in straightening the offset connector allowing for greater force to be displaced without creating fracture.

Flexibility: Often times in existing stents the tradeoff between flexibility and removability leaves one of these attributes with diminished performance. To achieve the requisite level of flexibility, the stent should have stent geometry that allows for inside and outside chord length changes. In order for this to happen, the cell design is usually weakened allowing the distortion or deflection to come from a shift in the cell geometry. In embodiments disclosed herein, the stent connectors are provided with an offset design, which lends itself to allowing these distortions to be displaced directly without significantly affecting the cell geometry. This provides a multitude of advantages: it allows the radial and indenter force to maintain consistency throughout a deflection, keeps indenter force high while allowing for a great deal of flexibility, prevents kinking/ovaling during deflection, and it also maintains the ability of the stent to be removed.

Embodiments of the stent described herein have the ability to axially extend or compress at least 20% or more of the stent's nominal deployed length without significantly altering the deployed diameter of the stent or suffering permanent deformation. In some embodiments, the stents described herein have the ability to axially extend or compress up to 40% or more of the nominal deployed length without significantly altering the deployed diameter of the stent or suffering permanent deformation.

In some embodiments, a tracheal stent comprises an expandable tubular member having a proximal end, a distal end, a longitudinal axis extending through the proximal and distal ends, an inner surface, and an outer surface. The stent comprises a plurality of strut columns and at least one connector extending between each strut column. The ends of the at least one connector are longitudinally and circumferentially offset from one another. In some embodiments the at least one connector extends from a peak of a strut pair of one strut column to a trough of a strut pair in a circumferentially adjacent strut column.

In some embodiments, the at least one connector comprises a first axial segment extending from a first end of a circumferential segment and second axial segment extending from a second end of the circumferential segment. In some embodiments the tracheal stent has a nominal state and an axially extended state. In at least one embodiment the tracheal stent has an axially shortened or compressed state.

In the nominal state the first axial segment and the circumferential segment define a nominal angle of about 90 degrees to about 115 degrees. In the axially extended state the first axial segment and the circumferential segment define an angle greater than that of the nominal angle. In the axially shortened state the first axial segment and the circumferential segment define an angle less than that of the nominal angle.

In at least one embodiment, in the axially extended state the first axial segment and the circumferential segment define an angle about 125 degrees to about 180 degrees.

In the nominal state the second axial segment and the circumferential segment define a nominal angle of about 90 degrees to about 115 degrees. In the axially extended state the second axial segment and the circumferential segment define an angle greater than that of the nominal angle. In the axially shortened state the second axial segment and the circumferential segment define an angle less than that of the nominal angle.

In at least one embodiment, in the axially extended state the second axial segment and the circumferential segment define an angle about 125 degrees to about 180 degrees.

In the various embodiments described herein a tracheal stent has a length. In the axially extended state the length is at least 20% greater than the length of the stent in the nominal state. In some embodiments when the stent is in the axially extended state the length is up to 40% greater than the length of the stent in the nominal state.

BRIEF DESCRIPTION OF THE DRAWINGS

FIG. 5 is a flat view of a portion of another embodiment of the stent.

DETAILED DESCRIPTION

Figure 1:
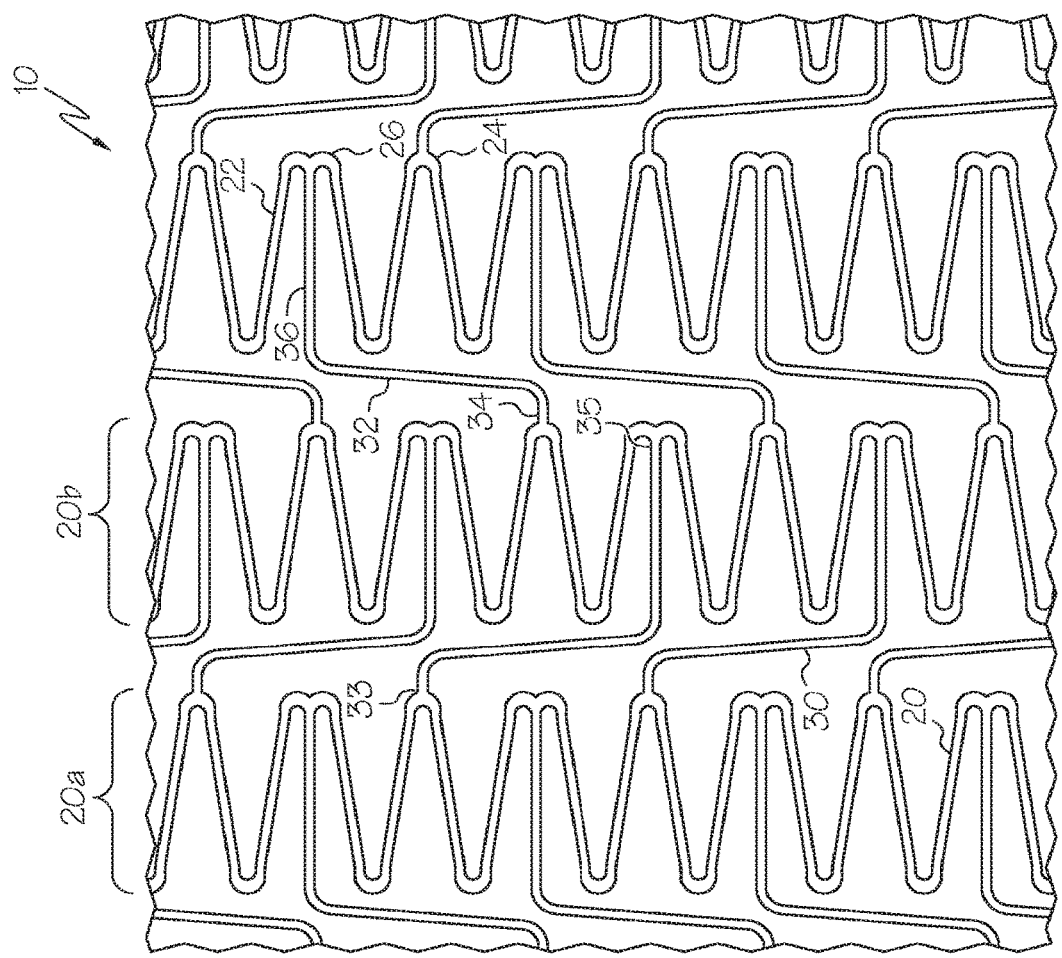
FIG. 1 is a flat view of a portion of a stent in a nominal state, according to one embodiment.

For the purposes of this disclosure, like reference numerals in the figures shall refer to like features unless otherwise indicated.

A partial view of a stent 10 is depicted in FIG. 1. In the embodiment shown, the stent 10 is depicted in a nominal deployed state. In an environment of use the nominal deployed or extended state of the stent 10 is a state wherein the outer surface of the stent is in contact with the trachea (not shown) of a patient, and the trachea is at rest (between inspiration and expiration events). Alternatively, the nominal deployed state can be defined as a state wherein the stent 10 is expanded to its programmed shape-memory deployed diameter.

As is shown in the various FIGS. 1-5, the stent 10 is comprised of a plurality of strut columns 20. Each strut column 20 is comprised of a series of interconnected struts 22 which form alternating peaks 24 and troughs 26. Adjacent strut columns 20 are connected by one or more connectors 30.

Each connector 30 is comprised of a circumferential segment 32 and first and second axial segments 34 and 36, which extend in substantially opposite directions from the opposing ends of the circumferential segment 32.

In the embodiments shown in FIGS. 1-4, a first (or proximal) end 33 of each connector 30 extends from a peak 24 of a first (or proximal) strut column 20a. A second (or distal) end 35 of each connector 30 extends from a trough 26 of a second (or distal) strut column 20b. In some embodiments the connectors 30 can extend from a trough 26 of the first strut column 20a and engage a peak 24 of the second strut column 20b such as in the manner depicted in FIG. 5.

In the various embodiments described herein, the length of the circumferential segment 32 results in the first and second axial segments 34 and 36 being circumferentially offset from one another in the nominal state. The length of the circumferential segment 32 is such that it extends in a circumferential direction across at least one trough 26 of the first strut column 20a and at least one peak 24 of the second strut column 20b. The length of the circumferential segment 32 can vary a great deal. For example, in the alternative embodiment shown in FIG. 5, the length of the circumferential segment 32 is sufficient to cross over six peaks 24 of the first strut column 20a and five troughs 26 of the second strut column 20b. Various other lengths and configurations of peak and trough crossings can be provided to the connectors 30.

Figure 3:
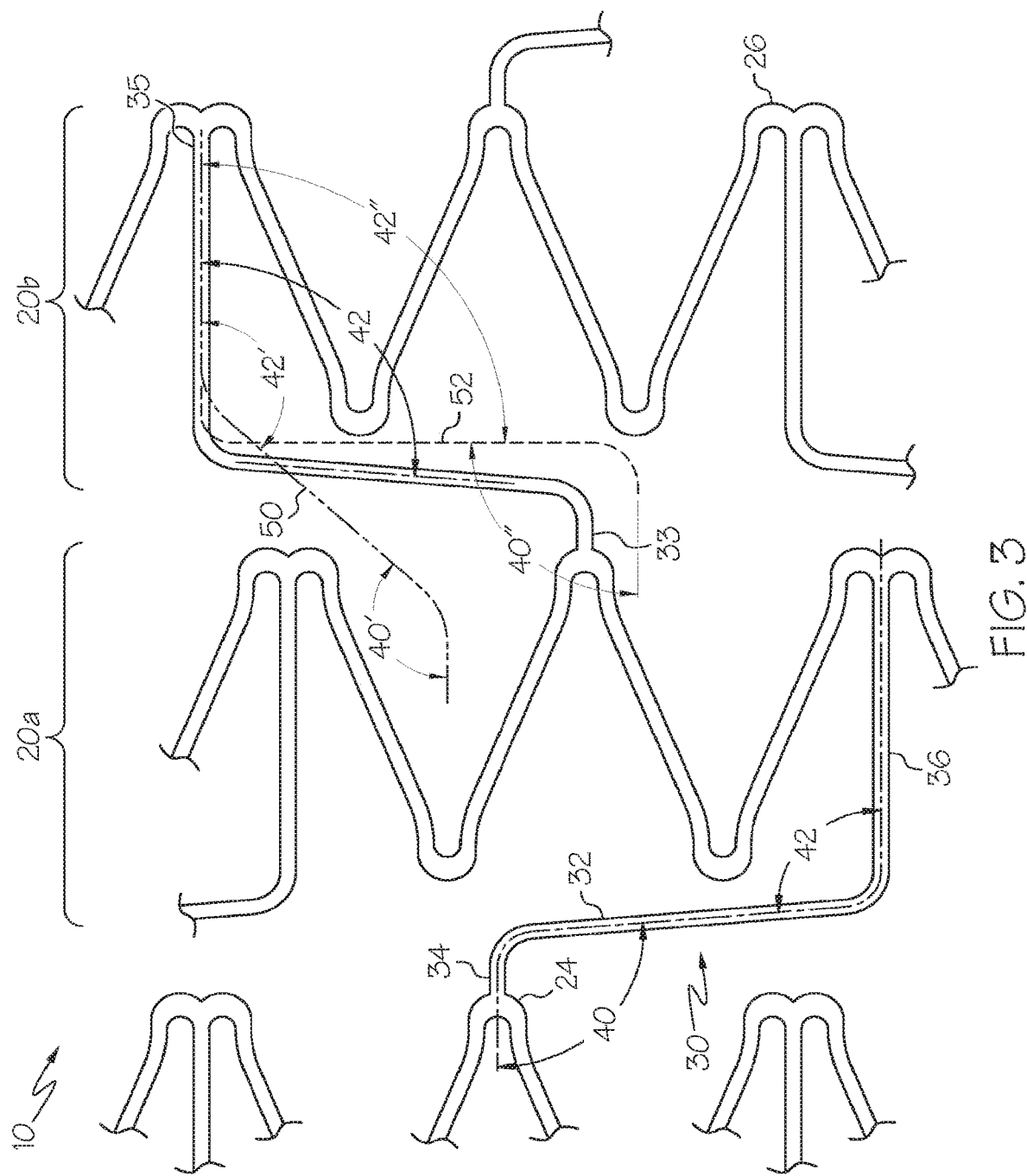
FIG. 3 is an annotated close-up view of a connector and adjacent strut columns of the stent shown in FIG. 1, wherein the annotations depict examples of configurations of the connector in an axially compressed state and an axially extended state, according to one embodiment.

In the nominally extended state shown the first axial segment 34 and the circumferential segment 32 define a nominal angle 40 of about 90 degrees to about 115 degrees, as shown in FIG. 3. Similarly, the second axial segment 36 and the circumferential segment 32 define a nominal angle 42 of about 90 degrees to about 115 degrees. In some embodiments angles 40 and 42 define alternate interior angles.

Figure 2:
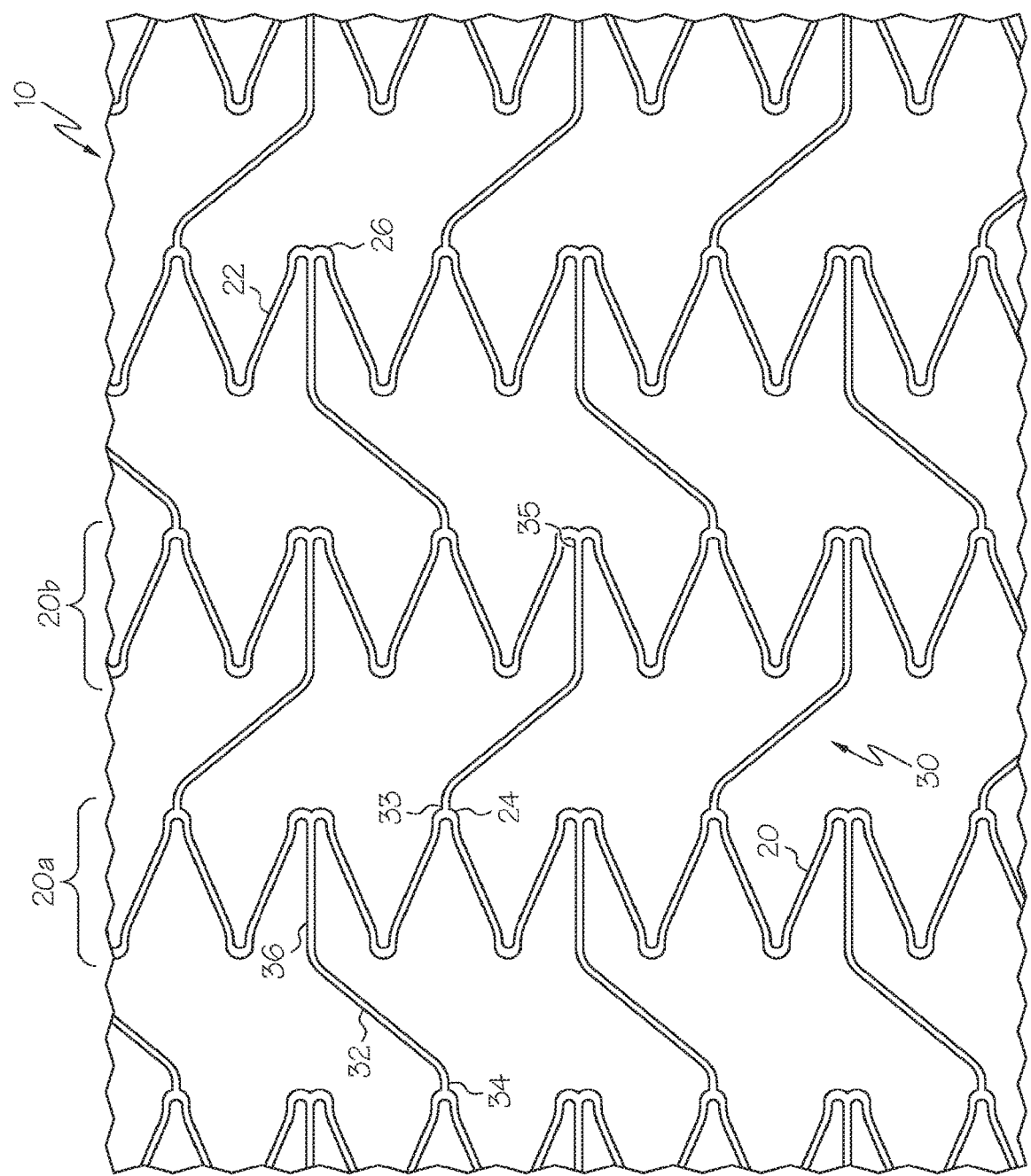
FIG. 2 is a flat view of the stent portion shown in FIG. 1 in an axially extended state, according to one embodiment.
Figure 4:
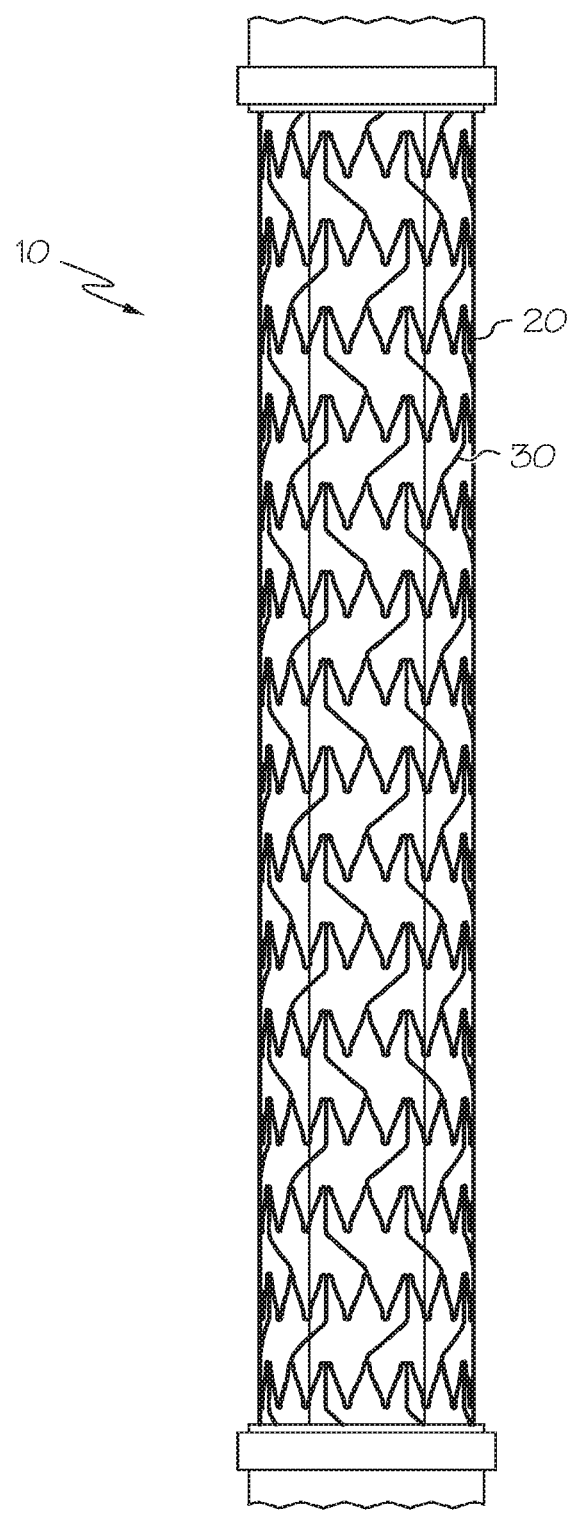
FIG. 4 illustrates the entire stent depicted in FIG. 1 in a laboratory setting with the stent in an axially extended state, according to one embodiment.

When deployed within the trachea, stent 10 is configured to be capable of extending from the nominally deployed state shown in FIG. 1 to an axially extended state, such as is shown in FIGS. 2 and 4. In the axially extended state the stent may have an axial length 20 percent greater (or more) than the length of the stent 10 in the nominally deployed state. As illustrated via FIG. 2, when the stent 10 is expanded to the axially extended state, deflection of the connectors 30 permits the stent 10 to axially elongate such that a majority of the axial elongation results from deflection of the connectors 30 rather than from distortions of the strut columns 20.

In the axially extended state the first axial segment 34 and the circumferential segment 32 define an angle 40' greater than that of the nominal angle 40. In at least one embodiment, in the axially extended state the first axial segment 34 and the circumferential segment 32 define an angle 40' of about 125 degrees to about 180 degrees. Likewise, in the axially extended state the second axial segment 36 and the circumferential segment 32 define an angle 42' greater than that of the nominal angle 42. In at least one embodiment, in the axially extended state the second axial segment 36 and the circumferential segment 32 define an angle 42' of about 125 degrees to about 180 degrees. In some embodiments angles 40' and 42' define alternate interior angles.

In addition to being capable of extending axially during an inspiration event, embodiments of the stent 10 are also configured to adapt to expiration events wherein the trachea may compress in the axial direction. An example of the extent to which a connector 30 can "extend" from the nominally deployed state to an axially extended state is illustrated by annotation line 50 and an example of the extent to which the connector 30 can compress from the nominally deployed state to an axially compressed state is shown by annotation line 52.

When the stent 10 is extended from the nominally deployed state (trachea at rest) to the axially extended state (inspiration), the connectors 30 (as represented by annotation line 50 in FIG. 3) will deflect such that the adjacent strut columns can move axially apart from one another (e.g. axially extend) without significantly affecting the deployed diameter of the stent 10. When the stent 10 is axially compressed (expiration) from the nominally deployed diameter (trachea at rest) in the axially compressed state, the connectors 30 (as represented by annotation line 52 in FIG. 3) will deflect such that the adjacent strut columns can move axially toward one another (e.g. axially compress) without significantly affecting the deployed diameter of the stent 10.

In the various embodiments shown and described herein, when the stent 10 is in the axially compressed or shortened state (as represented by annotation line 52 in FIG. 3), the first axial segment 34 and the circumferential segment 32 define an angle 40" that is less than that of the nominal angle 40. Similarly, in the axially compressed state the second axial segment 36 and the circumferential segment 32 define an angle 42" that is less than that of the nominal angle 42. In some embodiments angles 40" and 42" define alternate interior angles.

The unique geometry of the stent 10 provides the stent 10 with the capability to axially extend or compress by at least 20% or more of its nominal deployed length without significantly altering the deployed diameter of the stent or causing the stent to suffer permanent deformation. In some embodiments, the stent 10 is capable of axially extending or compressing by up to 40% of the nominal deployed length without significantly altering the deployed diameter of the stent or causing the stent to suffer permanent deformation.

In some embodiments a force necessary to change the length of the stent from a nominal length to an axially extended length is less than about 0.5 lbs. In at least one embodiment the force necessary to change the length of the stent from a nominal length to an axially extended length is about 0.472 lbs. In some embodiments a force necessary to change the length of the stent from a nominal length to an axially extended length is about 0.2 lbs to about 0.25 lbs.

In addition to the above it is recognized that any embodiments of the present stent 10 may be provided with a uniform diameter, may taper in portions or along the entire length of the stent, may have struts 20 and/or connectors 30 with uniform or different widths and/or thicknesses.

Embodiments of stent 10 may be manufactured using any appropriate stent manufacturing techniques. Appropriate methods for manufacturing the stents may include laser cutting, chemical etching or stamping of a tube. The stents may also be manufactured by laser cutting, chemically etching, stamping a flat sheet, rolling the sheet and welding the sheet, by electrode discharge machining, or by molding the stent with the desired design.

Any appropriate stent material may be used in the manufacture of the inventive stent 10. Examples of such materials may include polymeric materials, metals, ceramics and composites. Appropriate polymeric materials include thermotropic liquid crystal polymers (LCP's). Where the stent 10 is made of metal, the metal may be stainless steel, cobalt chrome alloys such as elgiloy, tantalum or other plastically deformable metals. Other suitable metals include shape-memory metals such as nickel-titanium alloys generically known as "nitinol", platinum/tungsten alloys and titanium alloys, stainless steel, tantalum and elgiloy. This disclosure also contemplates the use of more than one material in the manufacture of the stent 10. For example, first strut columns 20*a* and second strut columns 20*b* may be made of different materials. Optionally, the connectors 30 may be made of a different material than the strut columns 20.

Embodiments of the stent 10 are self-expanding. However in some embodiments the stent 10 may be provided in mechanically expandable form, in self- or as a hybrid of self-expanding and mechanically expandable. Mechanically expandable stents, in accordance with the disclosure, may be expanded using any suitable mechanical device.

Embodiments of the stent 10 may include suitable radiopaque coatings. For example, the stents may be coated with gold or other noble metals or sputtered with tantalum or other metals. The stents may also be made directly from a radiopaque material to obviate the need for a radiopaque coating or may be made of a material having a radiopaque inner core. Other radiopaque metals which may be used include platinum, platinum-tungsten, palladium, platinum-iridium, rhodium, tantalum, or alloys or composites of these metals.

Embodiments of the stent 10 may be provided with various bio-compatible coatings to enhance various properties of the stent. For example, the stents may be provided with lubricious coatings. The stents may also be provided with drug-containing coatings which release drugs over time.

Embodiments of the stent 10 may also be used as the framework for a graft, sleeve, covering or coating (partially or over the entire surface of the stent). Suitable coverings include but are not limited to, nylon, collagen, PTFE and expanded PTFE, polyethylene terephthalate and KEVLAR. More generally, any known graft material may be used including natural or synthetic polymers such as silicone, polyethylene, polypropylene, polyurethane (or urethane), polyglycolic acid, polyesters, polyamides, their mixtures, blends, copolymers, mixtures, blends and copolymers.

A description of some embodiments of the stents and the delivery catheter are contained in one or more of the following numbered statements:

Statement 1. A stent having a nominally deployed state, an axially extended state, and an axially compressed state, the stent having a length, in the axially extended state the length being at least 20% greater than in the nominally deployed state.

Statement 2. The stent of statement 1, wherein the stent is a tracheal stent.

Statement 3. The stent of any one of the preceding statements, wherein the stent is formed from a shape-memory metal.

Statement 4. The stent of any one of the preceding statements, wherein the stent is self-expanding.

Statement 5. The stent of any one of the preceding statements, wherein the stent is balloon-expandable.

Statement 6. The stent of any one of the preceding statements further comprising a radiopaque coating.

Statement 7. The stent of any one of the preceding statements further comprising a plurality of strut columns.

Statement 8. The stent of statement 7, wherein strut columns comprise columnar struts interconnected by alternating peaks and troughs.

Statement 9. The stent of statement 8 further comprising connector columns, the connector columns comprising connector struts extending between adjacent strut columns in a peak-to-trough configuration.

Statement 10. The stent of statement 9, wherein:

the connector struts comprise a first axial segment, a second axial segment, and a circumferential segment, the first axial segment and the second axial segment extending from the circumferential segment, the circumferential segment disposed between the first and second axial segments;

the first axial segment and the circumferential segment defining a first angle therebetween and the second axial segment and the circumferential segment defining a second angle therebetween, wherein:

when the stent is in the nominally deployed state the first angle is between 90 and 115 degrees and the second angle is between 90 degrees and 115 degrees;

when the stent is in the axially extended state the first angle is between 125 and 180 degrees and the second angle is between 125 and 180 degrees; and [0059] when the stent is in the axially compressed state, the first angle and second angle are less than when the stent is in the nominally deployed state.

Statement 11. The stent of any one of claims 7-10, wherein at least one of the strut columns is formed from a material different than at least one of the other strut columns.

Statement 12. The stent of statement 10, wherein the strut columns comprise first strut columns and second strut columns, the first and second strut columns comprising alternating peaks and troughs;

the circumferential segments extend in a circumferential direction across at least one trough of the first strut column and at least one peak of the second strut column.

Statement 13. The stent of statement 12, wherein the circumferential segments extend in a circumferential direction across at least one trough of the first strut column and at least two peaks of the second strut column.

Statement 14. The stent of any one of the preceding statements, wherein, in the axially extended state the length is up to 40% greater than in the nominally deployed state.

Statement 15. The stent of any one of the preceding statements, wherein at least a portion of the stent is formed from a nickel-titanium alloy.

Statement 16. The stent of any one of the preceding statements, wherein the stent is laser cut.

Statement 17. The stent of any one of statements 9, 10, 12, and 13, wherein the connector struts deflect when the stent is in the axially extended state and an axially compressed state.

The above disclosure describes using the stent 10 in the trachea. However, the disclosure may be used in any application involving expansion of a vessel (or support of a vessel wall) where a flow path on an outer surface of the stent is required, such as in the biliary duct and the duodenum.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to." Those familiar with the art may recognize other equivalents to the specific embodiments described herein which equivalents are also intended to be encompassed by the claims.

What is claimed is:

1. A stent, comprising:
   a tubular scaffold including a diameter and a plurality of strut columns alternating with a plurality of connector columns along a length of the stent;
   wherein each of the strut columns includes a plurality of interconnected struts extending circumferentially around a longitudinal axis of the stent, wherein the interconnected struts form alternating peaks and troughs;
   wherein the connector columns include a plurality of connector struts, wherein each of the connector struts includes a first axial segment coupled to a first peak of a first strut column, a second axial segment coupled to a first trough of a second strut column, and a circumferential segment extending in a single circumferential direction from the first axial segment to the second axial segment; and
   wherein the stent includes a first position having a first length and a second position having a second length, the second length being at least 20% greater than the first length;
   wherein the stent is configured to shift between the first length and the second length without a changing its diameter.

2. The stent of claim 1, wherein the first axial segment is circumferentially offset from the second axial segment.

3. The stent of claim 1, wherein the plurality of connector struts extend between adjacent strut columns in a peak-to-trough configuration.

4. The stent of claim 1, wherein the circumferential segment of each connector strut extends across at least one trough of the first strut column and at least two peaks of the second strut column.

5. The stent of claim 1, wherein the first axial segment has a first length and wherein the second axial segment has a second length, and wherein the second axial segment is longer than the first axial segment.

6. The stent of claim 1, wherein the stent includes a third position having a third length and wherein the third length is shorter than the first length.

7. The stent of claim 6, wherein the stent is configured to shift between the first length and the third length without changing its diameter.

8. The stent of claim 1, wherein at least one of the plurality of strut columns is formed from a material different from another of the plurality of strut columns.

9. The stent of claim 1, wherein at least one of the plurality of strut connectors is formed from a material different from the material used to construct the interconnected struts of at least one of the strut columns.

10. The stent of claim 1, wherein the first axial segment and the circumferential segment define a first angle therebetween, and wherein the second axial segment and the circumferential segment define a second angle therebetween, and wherein each of the first angle and the second angle is between 90 and 115 degrees when the stent is in the first position.

11. The stent of claim 1, wherein the first axial segment and the circumferential segment define a first angle therebetween, and wherein the second axial segment and the circumferential segment define a second angle therebetween, and wherein each of the first angle and the second angle is between 125 and 180 degrees when the stent is in the second position.

12. The stent of claim 1, wherein the first axial segment and the second axial segment define a circumferential distance extending therebetween, and wherein the circumferential distance shortens as the stent shifts from the first length to the second length.

13. A tracheal stent, comprising:
   a plurality of strut columns alternating with a plurality of connector columns along a longitudinal axis of the stent;
   wherein each of the strut columns includes a plurality of interconnected struts extending circumferentially around a longitudinal axis of the stent, wherein the interconnected struts form alternating peaks and troughs;
   wherein the connector columns include a plurality of connector struts, and wherein each of the connector struts includes a first axial segment coupled to a first peak of a first strut column, a second axial segment coupled to a first trough of a second strut column, and a circumferential segment extending only in a first circumferential direction from the first axial segment to the second axial segment;
   wherein the first axial segment is circumferentially offset from the second axial segment;
   wherein the stent is configured to shift between a nominally deployed configuration in which the stent has a nominally deployed length and an axially extended configuration in which the stent has an axially extended length, wherein the axially extended length is at least 20% greater than the nominally deployed length;

wherein the stent is configured to shift between an axially compressed configuration in which the stent has an axially compressed length to the axially extended configuration, wherein the axially compressed length is less than the nominally deployed length.

14. The stent of claim 13, wherein the stent is configured to shift between the axially compressed length and the axially extended length without changing its diameter.

15. The stent of claim 13, wherein the plurality of connector struts extend between adjacent strut columns in a peak-to-trough configuration.

16. The stent of claim 13, wherein the circumferential segment of each connector strut extends across at least one trough of the first strut column and at least two peaks of the second strut column.

17. The stent of claim 13, wherein the first axial segment has a first length and wherein the second axial segment has a second length, and wherein the second axial segment is longer than the first axial segment.

18. The stent of claim 13, wherein at least one of the plurality of strut columns is formed from a material different from another of the plurality of strut columns.

19. The stent of claim 13, wherein at least one trough is positioned between adjacent connector struts of the plurality of connector struts.

20. A tracheal stent, comprising:
a tubular scaffold including a diameter and a plurality of strut columns alternating with a plurality of connector columns along a length of the stent;
wherein each of the strut columns includes a plurality of interconnected struts extending circumferentially around a longitudinal axis of the stent, wherein the interconnected struts form alternating peaks and troughs;
wherein the connector columns include a plurality of connector struts, and wherein each of the connector struts includes a first axial segment coupled to a first peak of a first strut column, a second axial segment coupled to a first trough of a second strut column, and a circumferential segment extending from the first axial segment to the second axial segment;
wherein each circumferential segment within each connector column extends in only one circumferential direction from the first axial segment to the second axial segment;
wherein the stent includes a first position having a first length and a second position having a second length, and a third position having a third length, the third length being at least 20% greater than the second length and the second length being greater than the first length;
wherein the stent is configured to shift between the first length and the third length without a changing its diameter.

\* \* \* \* \*